US012616437B2

(12) United States Patent
Matsuki et al.

(10) Patent No.: US 12,616,437 B2
(45) Date of Patent: May 5, 2026

(54) X-RAY IMAGING APPARATUS

(71) Applicant: SHIMADZU CORPORATION, Kyoto (JP)

(72) Inventors: Daisuke Matsuki, Kyoto (JP); Junya Yamamoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 18/699,162

(22) PCT Filed: Nov. 25, 2021

(86) PCT No.: PCT/JP2021/043203

§ 371 (c)(1),
(2) Date: Apr. 5, 2024

(87) PCT Pub. No.: WO2023/095245

PCT Pub. Date: Jun. 1, 2023

(65) Prior Publication Data

US 2024/0407748 A1     Dec. 12, 2024

(51) Int. Cl.
*A61B 6/00*          (2024.01)
*G06V 10/764*        (2022.01)

(52) U.S. Cl.
CPC ............ *A61B 6/545* (2013.01); *A61B 6/5205* (2013.01); *A61B 6/5211* (2013.01); *G06V 10/764* (2022.01); *G06V 2201/03* (2022.01)

(58) Field of Classification Search
CPC ....... A61B 6/405; A61B 6/545; A61B 6/5205; A61B 6/5211; G06V 2201/03; G06V 10/764
See application file for complete search history.

(56) References Cited

U.S. PATENT DOCUMENTS

| | | | | |
|---|---|---|---|---|
| 2008/0025586 | A1* | 1/2008 | Baumgart | G06T 5/92 |
| | | | | 382/128 |
| 2017/0281101 | A1* | 10/2017 | Choi | H05G 1/02 |
| 2020/0074632 | A1* | 3/2020 | Heindl | G16H 30/20 |
| 2021/0110584 | A1* | 4/2021 | Claessen | G06T 11/008 |

FOREIGN PATENT DOCUMENTS

| | | | | |
|---|---|---|---|---|
| EP | 3494884 A1 * | 6/2019 | | A61B 6/405 |
| JP | 6737337 B2 | 7/2020 | | |

OTHER PUBLICATIONS

Written Opinion by the International Searching Authority dated Jan. 25, 2022, for PCT application No. PCT/JP2021/043203.

* cited by examiner

*Primary Examiner* — John D Li
(74) *Attorney, Agent, or Firm* — Muir Patent Law, PLLC

(57)          ABSTRACT
This X-ray imaging device has an X-ray source, an X-ray detector, an image generation unit for generating an X-ray image, a site acquisition unit for acquiring a region for each site in the X-ray image based on a trained model, a region-of-interest selection unit for selecting a region-of-interest, and an X-ray condition adjustment unit to adjust the conditions of X-rays emitted from the X-ray source based on a first pixel value that a pixel value in the region-of-interest.

11 Claims, 9 Drawing Sheets

21b

30

Imaging region selection

| | | |
|---|---|---|
| 21a — Head and neck | Cervical spine | Abdomen — 21c |
| 21d — Chest | Hip joint | Leg — 21f |

21e

X-ray image

Site selection

22a — Bone tissue

Soft tissue — 22b

22c — Artifact

Background — 22d

FIG. 7

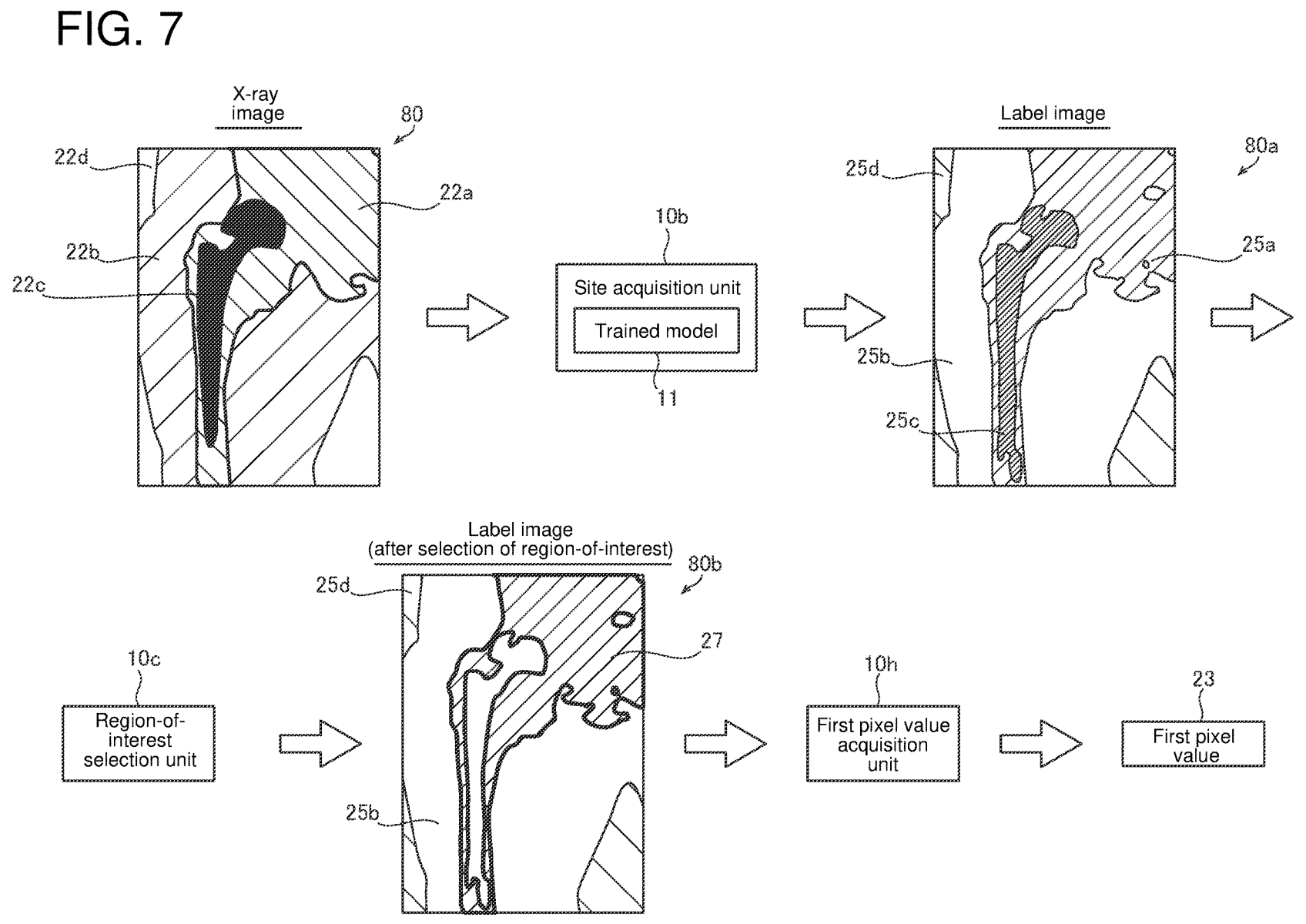

X-ray image

Label image

Site acquisition unit

Trained model

Label image (after selection of region-of-interest)

Region-of-interest selection unit

First pixel value acquisition unit

First pixel value

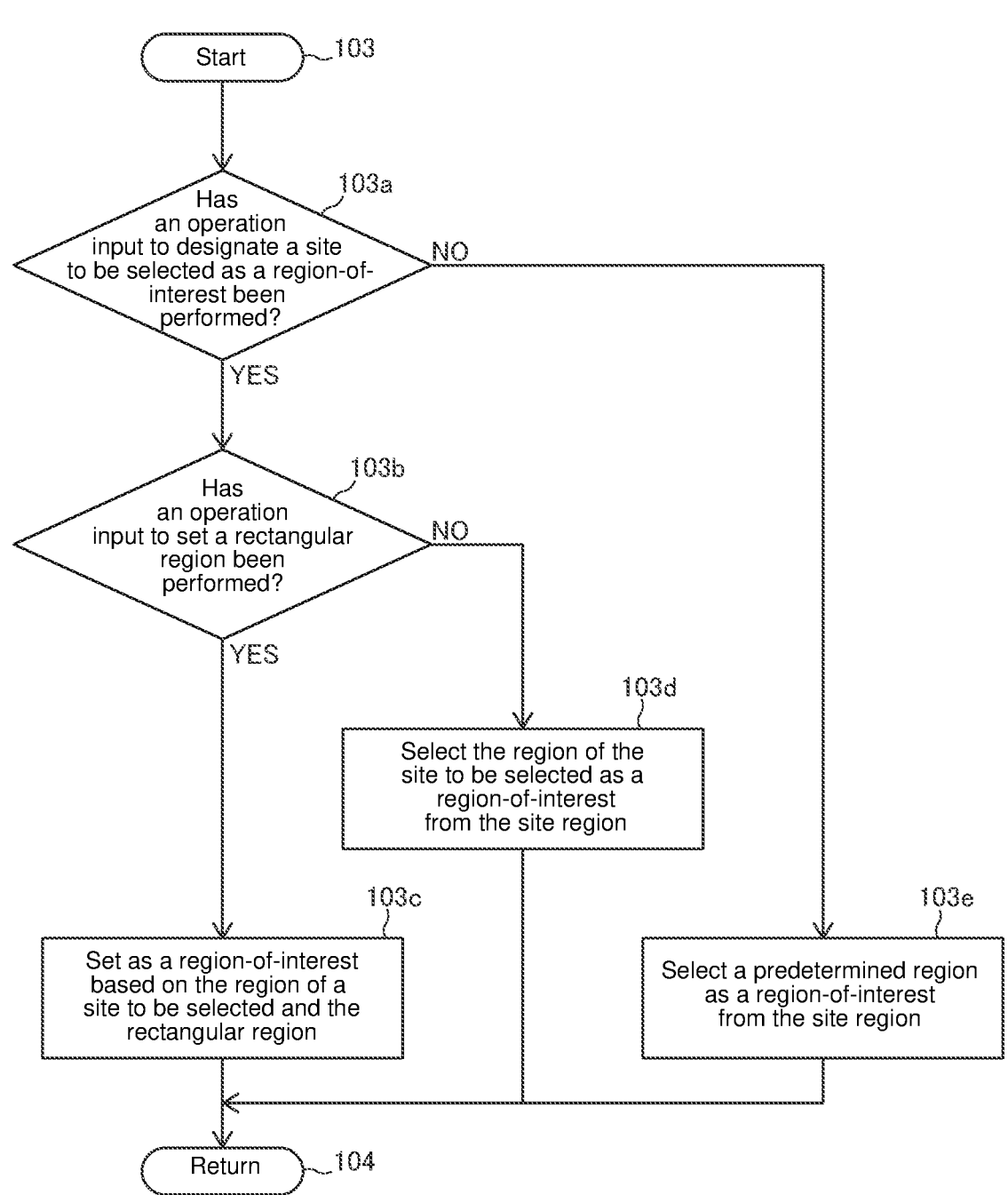

Region-of-interest
setting processing

Start — 103

Has
an operation
input to designate a site
to be selected as a region-of-
interest been
performed?　103a

NO

YES

Has
an operation
input to set a rectangular
region been
performed?　103b

NO

YES

103d
Select the region of the
site to be selected as a
region-of-interest
from the site region 103c
Set as a region-of-interest
based on the region of a
site to be selected and the
rectangular region 103e
Select a predetermined region
as a region-of-interest
from the site region Return — 104

X-RAY IMAGING APPARATUS

TECHNICAL FIELD

The present invention relates to an X-ray imaging apparatus, and more particularly to an X-ray imaging apparatus capable of performing imaging by adjusting X-ray conditions.

BACKGROUND ART

Conventionally, with regard to an X-ray imaging apparatus, in particular, there is known an X-ray imaging apparatus that performs imaging by adjusting the X-ray conditions. Such an X-ray imaging apparatus is disclosed, for example, in Japanese Patent No. 6737337.

The X-ray fluoroscopic imaging apparatus disclosed in Japanese Patent No. 6737337 is equipped with an X-ray tube, an X-ray detector, an image generation unit, and a controller. The controller is equipped with a region-of-interest setting unit for setting the region-of-interest on an X-ray image generated by the image generation unit and an irradiation condition automatic adjustment unit for calculating the X-ray irradiation conditions based on the luminance of the region-of-interest. The region-of-interest setting unit is configured to set a rectangular-shaped region-of-interest on the X-ray image. Further, the irradiation condition automatic adjustment unit is configured to compare the image luminance value within the rectangular-shaped region-of-interest with a predetermined ideal luminance value and to calculate the X-ray irradiation conditions so that the luminance value of the X-ray image becomes the ideal luminance value.

PRIOR ART DOCUMENT

Patent Document

Patent Document 1: Japanese Patent No. 6737337

SUMMARY OF THE INVENTION

Problems to be Solved by the Invention

Here, although not disclosed in Japanese Patent No. 6737337, it may happen that an X-ray image may capture various sites, such as, e.g., bones and internal organs. Therefore, as disclosed in Japanese Patent No. 6737337, when setting up a rectangular-shaped region-of-interest, multiple sites may be included within the region-of-interest. In this case, in some cases, sites other than the site that the user desires to visually recognize may be included in the region-of-interest. In the case where sites other than the site that the user desires to visually recognize are included in the region-of-interest, there are cases where the X-ray irradiation conditions (X-ray conditions) are not suitable for the site that the user desires to visually recognize due to the difference between the X-ray absorption rate at the site that the user desires to visually recognize and the X-ray absorption rate at the other sites. In this case, the inconvenience of reduced visibility of the site that the user desires to visually recognize occurs. For this reason, there is a need for an X-ray imaging apparatus capable of suppressing the deterioration of visibility of the site that the user desires to visually recognize by enabling the user to easily adjust the X-ray imaging conditions to suit the site that the user desires to visually recognize.

The present invention has been made to solve the above-mentioned problem. The purpose of the present invention is to provide an X-ray imaging apparatus capable of suppressing a decrease in visibility of a site that a user desires to visually recognize by enabling the user to easily adjust X-ray conditions to suit the site that the user desires to visually recognize.

Means for Solving the Problems

In order to attain the above-described objects, an X-ray imaging apparatus according to one aspect of the present invention includes:

an X-ray source configured to irradiate a patient with X-rays;

an X-ray detector configured to detect the X-rays emitted from the X-ray source;

an image generation unit configured to generate an X-ray image based on a detection signal of the X-rays detected by the X-ray detector; and a site acquisition unit configured to acquire a region for each site in the X-ray image, based on a trained model that has been trained to classify sites captured in the X-ray image;

a region-of-interest selection unit configured to select a region-of-interest from a region of the site acquired by the site acquisition unit; and an X-ray condition adjustment unit configured to adjust conditions of X-rays emitted from the X-ray source, based on a first pixel value that is a pixel value inside the region-of-interest selected by the region-of-interest selection unit.

Effects of the Invention

The X-ray imaging apparatus according to the above-described first aspect is provided with, as described above, a site acquisition unit configured to acquire a region for each site in an X-ray image, based on a trained model, a region-of-interest selection unit configured to select a region-of-interest from a region of a site acquired by the site acquisition unit, and an X-ray condition adjustment unit configured to adjust conditions of X-rays emitted from the X-ray source, based on a first pixel value that is a pixel value in the region-of-interest selected by the region-of-interest selection unit.

With this, the X-ray conditions are adjusted based on the first pixel value that is a pixel value in the region-of-interest among regions classified for each of a plurality of sites reflected in the X-ray image. Therefore, it is possible to suppress the inclusion of pixel values of sites other than the region-of-interest in the first pixel value. Therefore, it becomes possible to adjust the X-ray conditions based solely on the first pixel value, thereby making it easier to adjust the X-ray conditions to suit the site that the user desires to visually recognize. As a result, by enabling the user to easily adjust the X-ray conditions to suit the site that the user desires to visually recognize, it is possible to prevent the deterioration of the visibility of the site that the user desires to visually recognize.

BRIEF DESCRIPTION OF THE DRAWINGS

FIG. 5 is a schematic diagram describing a site selection screen for selecting a site in the X-ray imaging apparatus according to one embodiment.

FIG. 7 is a schematic diagram describing the configuration for a processor according to one embodiment to select a region-of-interest based on a preset site and acquire a first pixel value.

FIG. 8 is a schematic diagram describing the configuration for a processor according to one embodiment to set a region-of-interest based on a user's operation input and acquire a first pixel value.

FIG. 10 is a flowchart describing the processing for a processor according to one embodiment to acquire a region-of-interest.

EMBODIMENTS FOR CARRYING OUT THE INVENTION (Configuration of X-Ray Imaging Apparatus)

Figure 1:
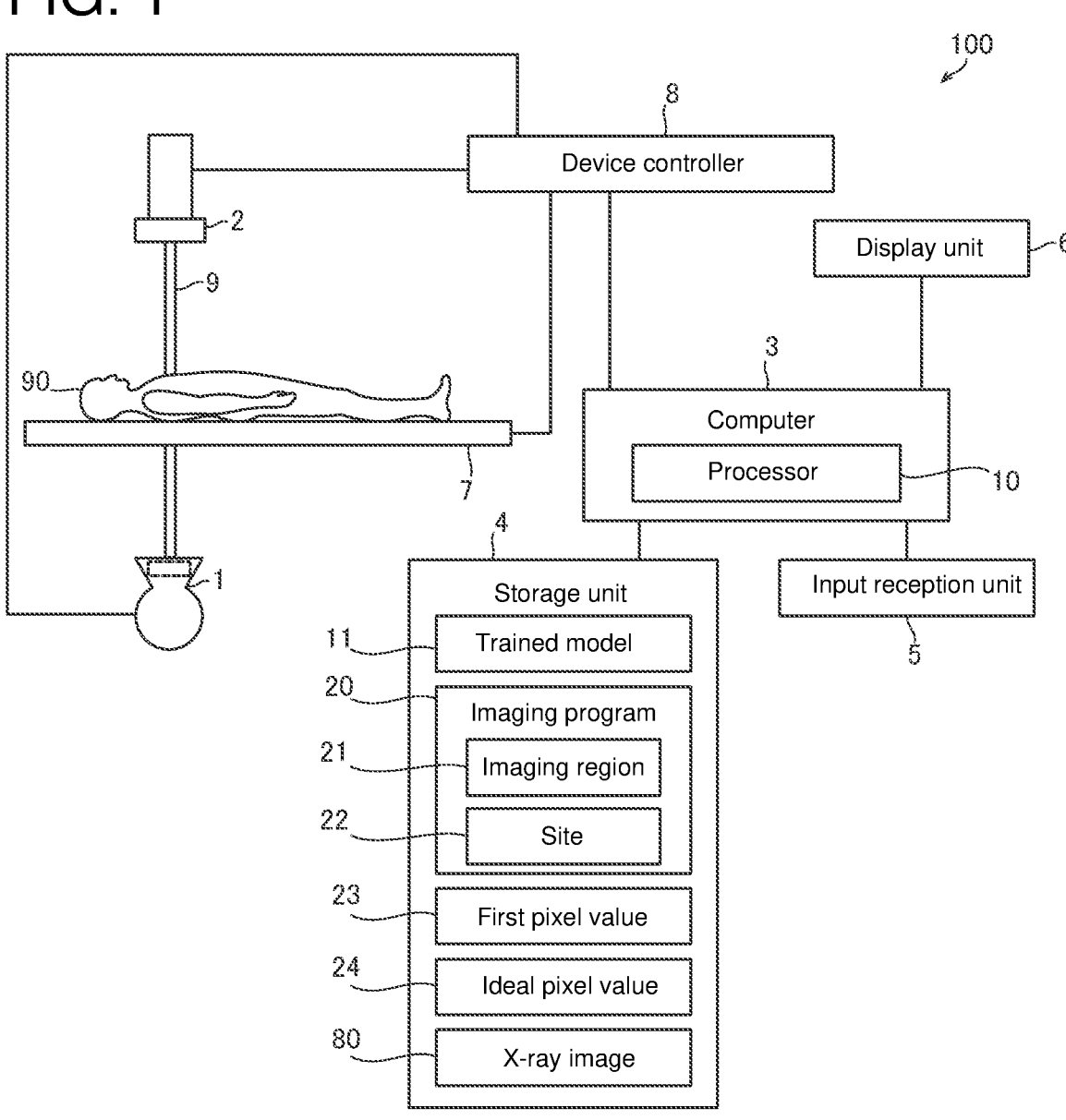
FIG. 1 is a diagram showing the entire configuration of an X-ray imaging apparatus according to one embodiment.

Referring to FIG. 1, the configuration of an X-ray imaging apparatus 100 according to one embodiment of the present invention will be described.

As shown in FIG. 1, the X-ray imaging apparatus 100 is equipped with an X-ray source 1, an X-ray detector 2, and a computer 3. The X-ray imaging apparatus 100 is further equipped with a storage unit 4. The X-ray imaging apparatus 100 is further equipped with an input reception unit 5. Furthermore, the X-ray imaging apparatus 100 is equipped with a display unit 6, a top board 7, and a device controller 8. In this embodiment, the X-ray imaging apparatus 100 images a patient 90 as a subject. The X-ray imaging apparatus 100 captures X-ray images 80 as a moving image, for example, at a predetermined frame rate. The X-ray imaging apparatus 100 is a so-called X-ray fluoroscopic imaging apparatus, which is installed in an operating room where a catheter treatment and other procedures are performed.

The X-ray source 1 and the X-ray detector 2 are held by an arm 9, which arranges the X-ray source 1 and the X-ray detector 2 to face each other. The arm 9 is a so-called C-arm. Further, the arm 9 is mounted on an arm moving mechanism (not illustrated) and is configured to be movable.

The X-ray source 1 is configured to irradiate the patient 90 with X-rays. Specifically, the X-ray source 1 emits X-rays when a voltage is applied by a drive unit, which is not illustrated. The X-ray source 1 has a collimator that can adjust the irradiation field, which is the X-ray irradiation range. In this embodiment, the X-ray source 1 is attached to the one side tip end of the arm 9.

The X-ray detector 2 is configured to detect X-rays emitted from the X-ray source 1. In this embodiment, the X-ray detector 2 is attached to the other side tip end of the arm 9. In other words, the X-ray detector 2 is arranged on a side opposite to the X-ray source 1 across the top board 7. Further, the X-ray detector 2 is configured to detect X-rays. The X-ray detector 2 is, for example, an FPD (Flat Panel Detector). The X-ray detector 2 is configured to detect X-rays that have passed through the subject (patient 90) and to output a detection signal based on the detected X-rays.

The computer 3 is configured to include a processor 10, such as, e.g., a CPU (Central Processing Unit), a GPU (Graphics Processing Unit), and an FPGA (Field-Programmable Gate Array) configured for image processing, a ROM (Read Only Memory), and a RAM (Random Access Memory).

The storage unit 4 is configured to store the X-ray image 80 acquired by the image generation unit 10a (see FIG. 2), as will be described later. Further, the storage unit 4 is configured to store various programs to be executed by the processor 10. Further, the storage unit 4 is configured to store an imaging program 20 for imaging the patient 90. Further, the storage unit 4 is configured to store a first pixel value 23 and an ideal pixel value 24, which are used when adjusting the X-ray conditions. The storage unit 4 includes a non-volatile storage unit, such as, e.g., an HDD (Hard Disk Drive) and an SSD (Solid State Drive).

The imaging program 20 is information in which the imaging region 21 of the patient 90 and a region of a site 22 (see FIG. 6) set in advance as a region-of-interest 27 (see FIG. 6) are associated with each other. In other words, the storage unit 4 stores the imaging region 21 of the patient 90 and the region 25 of the site 22 set in advance as the region-of-interest 27 in an associated state.

The ideal pixel value 24 is an ideal pixel value set in advance for each of the imaging regions 21 of the patient 90.

The input reception unit 5 is configured to receive an operation input from the user. The input reception unit 5 includes, for example, an input device, such as, e.g., a mouse, a keyboard, and a touch panel.

The display unit 6 is configured to display the X-ray image 80. Further, the display unit 6 is configured to display an operation screen for the user to operate the X-ray imaging apparatus 100. The display unit 6 includes, for example, a display device such as an LCD monitor. In this embodiment, the X-ray imaging apparatus 100 is equipped with a touch panel display integrating the input reception unit 5 and the display unit 6.

As shown in FIG. 1, the top board 7 is formed into a rectangular flat plate shape in plan view. The patient 90 is laid on the top board 7 so that the head-foot direction of the patient 90 is along the long side of the rectangle and that the left-right direction of the patient 90 is along the short side of the rectangle.

The top board 7 is provided with a moving mechanism (not illustrated). The X-ray imaging apparatus 100 can image the subject (patient 90) while changing the relative position between the top board 7 and the X-ray source 1 and the X-ray detector 2 by moving the top board 7 in the longitudinal direction with a moving mechanism.

The device controller 8 is configured to control the X-ray imaging apparatus 100. Specifically, the device controller 8 is configured to perform the control of the X-ray irradiation from the X-ray source 1, the control of the movement of the top board 7, and the control of the movement of the arm 9. Further, the device controller 8 is configured to control the X-ray dose output from the X-ray source 1 by controlling the X-ray source 1 by the input signals from the X-ray condition adjustment unit 10d (see FIG. 2), which will be described below.

The X-ray imaging apparatus 100 according to this embodiment moves the top board 7 and the arm 9 when the imaging region 21 is selected by the user. The X-ray imaging apparatus 100 initiates imaging when the operation to start imaging is performed. Thereafter, the X-ray imaging apparatus 100 adjusts the X-ray conditions based on the X-ray image 80. Note that in the case where the site 22 that is desired to be visually recognized is selected by the user, the X-ray imaging apparatus 100 adjusts the X-ray conditions so that the X-ray conditions are appropriate for the site 22 that is desired to be visually recognized by the user.

\<Functional Blocks Included in Processor>

Figure 2:
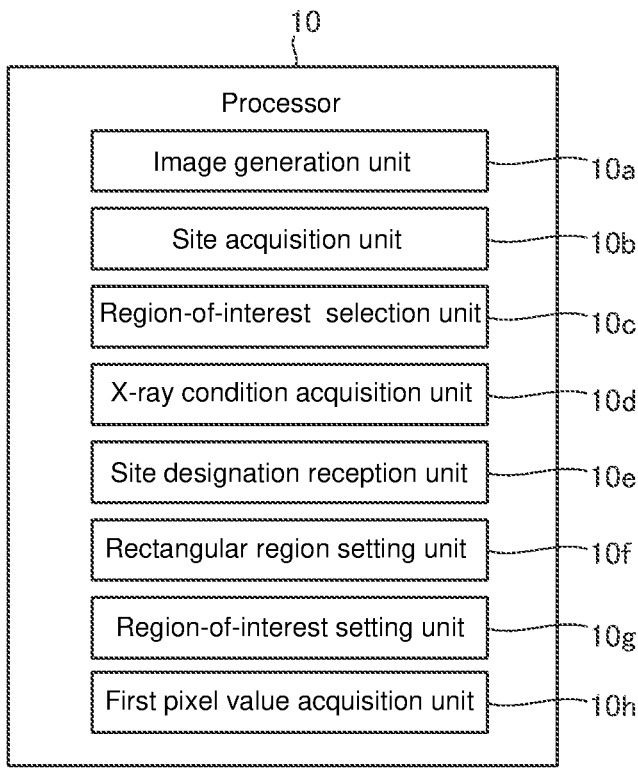
FIG. 2 is a block diagram describing the functional blocks provided by a processor according to one embodiment.

As shown in FIG. 2, the processor 10 includes an image generation unit 10*a*, a site acquisition unit 10*b*, a region-of-interest selection unit 10*c*, and an X-ray condition adjustment unit 10*d*. Further, in this embodiment, the processor 10 further includes a site designation reception unit 10*e*, a rectangular region setting unit 10*f*, a region-of-interest setting unit 10*g*, and a first pixel value acquisition unit 10*h*. The image generation unit 10*a*, the site acquisition unit 10*b*, the region-of-interest selection unit 10*c*, the X-ray condition adjustment unit 10*d*, the site designation reception unit 10*e*, the rectangular region setting unit 10*f*, the region-of-interest setting unit 10*g*, and the first pixel value acquisition unit 10*h* are configured in software as functional blocks realized by the processor 10 by executing various programs. The image generation unit 10*a*, the site acquisition unit 10*b*, the region-of-interest selection unit 10*c*, the X-ray condition adjustment unit 10*d*, the site designation reception unit 10*e*, the rectangular region setting unit 10*f*, the region-of-interest setting unit 10*g*, and the first pixel value acquisition unit 10*h* may be configured by hardware by providing a dedicated processor (processing circuit). The details of each functional block included in the processor 10 will be described below.

\<Imaging Region Selection Screen>

Next, referring to FIG. 3, the imaging region selection screen 30 will be explained when the user selects the imaging region 21 (see FIG. 1).

The imaging region selection screen 30 is a screen displayed on the display unit 6 (see FIG. 1) when the user selects the imaging region 21 (see FIG. 1) before the user starts imaging.

In the imaging region selection screen 30, buttons for selecting each of the imaging regions 21 are displayed. In the example shown in FIG. 3, displayed are buttons for selecting a head and neck 21*a*, a cervical spine 21*b*, an abdomen 21*c*, a chest 21*d*, a hip joint 21*e*, and a leg 21*f* as each of the imaging regions 21. Note that each button for selecting the imaging region 21 is a push button displayed on the GUI (Graphical User Interface).

When one of the buttons displayed on the imaging region selection screen 30 is operated (pressed) by the user, the processor 10 (see FIG. 1) moves at least one of the top board 7 (see FIG. 1) and the arm 9 (see FIG. 1) to the preset position according to the selected imaging region 21. Thereafter, when the user performs an operation input to start imaging, imaging is initiated.

\<X-Ray Image>

Next, the X-ray image 80 that the image generation unit 10*a* (see FIG. 2) generates will be described with reference to FIG. 4. The example shown in FIG. 4 shows an X-ray image 80 which shows the captured image of the hip joint of the patient 90 (see FIG. 1) when the hip joint 21*e* (see FIG. 3) is selected as the imaging region 21 (see FIG. 1) by the imaging region selection screen 30 (see FIG. 3).

Figures 3, 4:
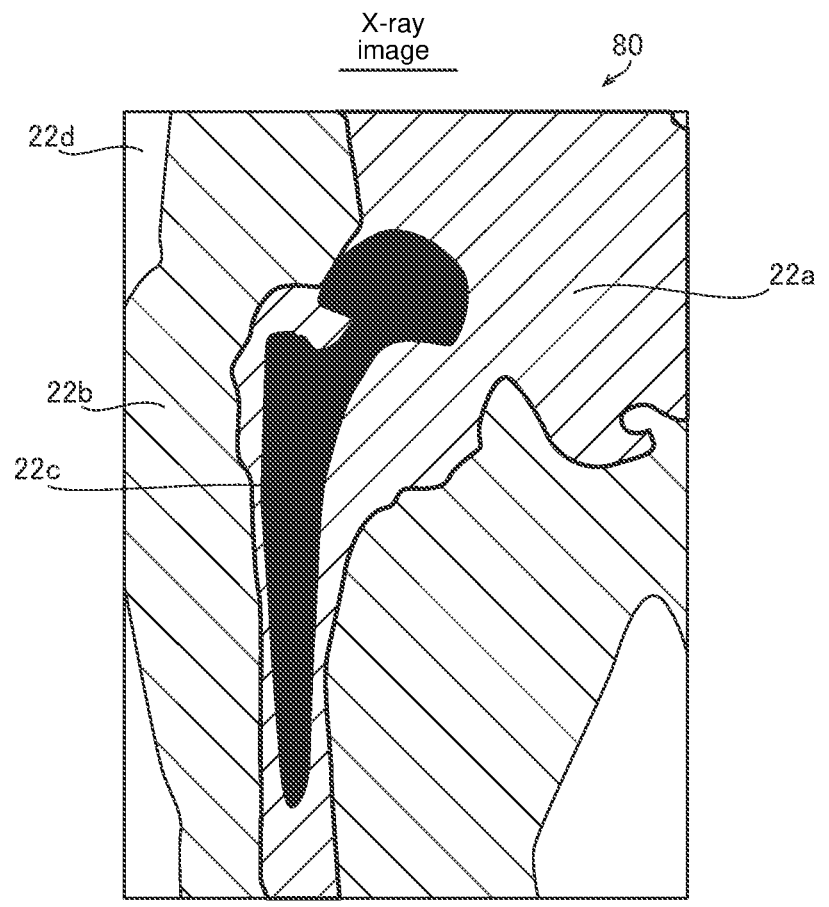
FIG. 3 is a schematic diagram describing an imaging region selection screen for selecting an imaging region in the X-ray imaging apparatus according to one embodiment.
FIG. 4 is a schematic diagram describing an X-ray image generated by an image generation unit according to one embodiment.

In the X-ray image 80 shown in FIG. 4, multiple sites 22 (see FIG. 1) are captured. The multiple sites 22 include, for example, bone tissues 22*a*, soft tissues 22*b*, such as skins and muscles, and backgrounds 22*d*. Further, FIG. 4 shows an example in which the patient 90 is imaged with an artifact 22*c* placed in a bone tissue 22*a*, so the site 22 includes the artifact 22*c*. The artifact 22*c* includes, for example, metallic materials, ceramics, etc. In the example shown in FIG. 4, the artifact 22C is a metal artificial bone. Note that the X-ray image 80 shown in FIG. 4 has different hatching for the bone tissue 22*a*, the soft tissue 22*b*, the artifact 22*c*, and the background 22*d*, in order to distinguish between them.

The processor 10 (see FIG. 1) adjusts the X-ray conditions when sequentially capturing X-ray images 80 capturing a plurality of sites 22, as shown in FIG. 4. The X-ray conditions include at least a tube voltage. Note that the X-ray conditions include, in addition to the tube voltage, the tube current, and the X-ray irradiation time. In this embodiment, the configuration for the processor 10 to adjust the X-ray conditions by changing the value 12 (see FIG. 6) of the tube voltage will be described.

\<Site Selection Screen>

Next, referring to FIG. 5, the site selection screen 31 used to select the site 22 (see FIG. 1) that the user desires to visually recognize will be described.

Figure 5:
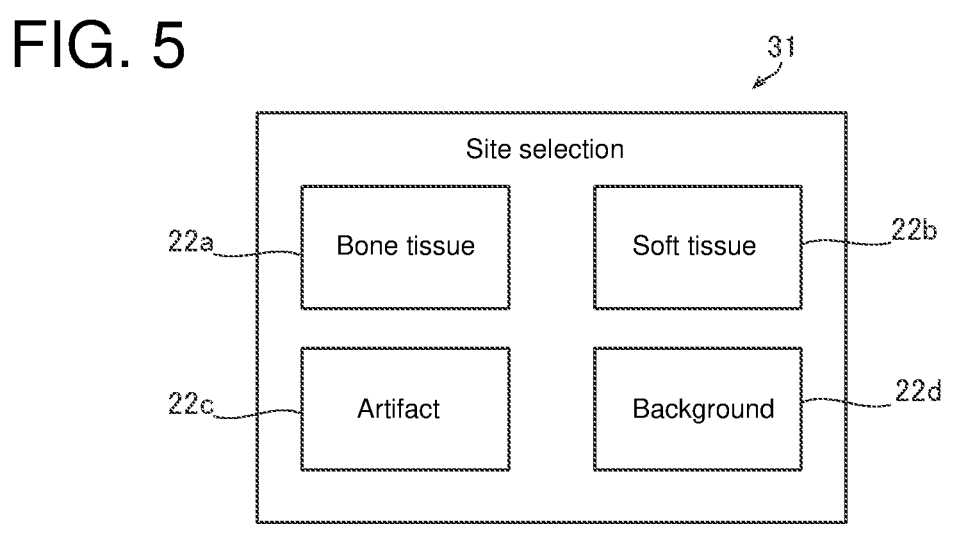

The site selection screen 31 shown in FIG. 5 is a screen for selecting a site 22 (see FIG. 1) that the user desires to visually recognize among the sites 22 (see FIG. 1) in the imaging region 21 (see FIG. 1). Specifically, the site selection screen 31 is a screen for selecting a site 22 desired to be visually recognized when a site 22 other than a preset site 22 is desired to be visually recognized. That is, the site selection screen 31 is displayed on the display unit 6 (see FIG. 1) after the selection of the imaging region 21 on the imaging region selection screen 30 (see FIG. 3).

The site selection screen 31 displays buttons for selecting a site 22 (see FIG. 1) that the user desires to visually recognize among the sites 22 (see FIG. 4) that appear in the X-ray image 80 (see FIG. 4). In the example shown in FIG. 5, buttons for selecting a bone tissue 22*a*, a soft tissue 22*b*, an artifact 22*c*, and a background 22*d* are displayed as each site 22. Note that each button for selecting a site 22 is a pushbutton displayed in a GUI.

When any of the buttons displayed on the site selection screen 31 is operated (pressed) by the user, the processor 10 (see FIG. 1) adjusts the X-ray conditions to suit the selected site 22.

Note that the storage unit 4 (FIG. 1) stores an imaging program 20 (FIG. 1) in which the imaging region 21 (FIG. 1) of the patient 90 and the region 25 (see FIG. 6) of the site 22 (FIG. 4) set in advance as the region-of-interest 27 (FIG. 6) are associated. Therefore, in the case where there is no input operation on the site selection screen 31, the processor 10 adjusts the X-ray conditions so that the X-ray conditions are suitable for the preset site 22 based on the imaging region 21 selected by the imaging region selection screen 30 (see FIG. 3) and the imaging program 20.

\<Adjustment of X-Ray Conditions>

Next, referring to FIG. 6, the configuration for the processor 10 to adjust the X-ray conditions will be described. The processor 10 sets one region 25 out of a plurality of sites 22 captured in the X-ray image 80 as a region-of-interest 27 and adjusts the X-ray conditions based on the pixel values of the region-of-interest 27. In the configuration for the processor 10 to adjust the X-ray conditions, the configuration for setting the region-of-interest 27 includes the following three configurations:

(1) A first configuration in which a region 25 of a site 22 set in advance among the sites 22 (see FIG. 4) that appear in the X-ray image 80 generated by the image generation unit 10*a* is set as a region-of-interest 27.

(2) A second configuration in which a region 25 (region 25*e* to be selected as a region-of-interest 27) of a site 22*e* to be selected as a region-of-interest 27 selected by the user's operation input is set as a region-of-interest 27.

(3) A third configuration in which a region-of-interest 27 is set based on a region 25 of a site 22 set in advance, or a region 25*e* to be set as a region-of-interest 27, and a rectangular region 26 selected by the user is set as a region-of-interest 27.

Hereinafter, the details of each configuration for the processor 10 to adjust the X-ray conditions will be described.

First, the first configuration for the processor 10 to set the region-of-interest 27 will be described. The image generation unit 10*a* acquires an X-ray detection signal from the X-ray detector 2 (see FIG. 1). The image generation unit 10*a* generates an X-ray image 80 based on the X-ray detection signal detected by the X-ray detector 2. Further, the image generation unit 10*a* outputs the generated X-ray image 80 to the site acquisition unit 10*b*. Note that the image generation unit 10*a* may store the generated X-ray image 80 in the storage unit 4.

The site acquisition unit 10*b* acquires the X-ray image 80 from the image generation unit 10*a*. Further, the site acquisition unit 10*b* reads a trained model 11 from the storage unit 4. The site acquisition unit 10*b* acquires the region 25 for each site 22 (FIG. 4) captured in the X-ray image 80 (FIG. 4), based on the X-ray image 80 input image from the image generation unit 10*a* and the trained model 11 read from the storage unit 4.

Note that in this embodiment, the trained model 11 is generated by learning to classify the sites 22 (see FIG. 1) captured in the X-ray image 80, and has been stored in advance in the storage unit 4. In this embodiment, the trained models 11 include a plurality of trained models 11 for each imaging region 21 (see FIG. 1) that have been trained to classify the sites 22 according to the imaging region 21 (see FIG. 1).

In this embodiment, the site acquisition unit 10*b* is configured to acquire the region 25 of the site 22 in the X-ray image 80, based on the trained model 11 corresponding to the imaging region 21 out of the plurality of trained models 11. In this embodiment, the site acquisition unit 10*b* is configured to acquire, as the region 25 of the site 22, at least two of the following regions: the region 25*a* of the bone tissue 22*a*, the region 25*b* of the soft tissue 22*b*, the region 25*c* of the artifact 22*c*, and the region 25*d* of the background 22*d*, as illustrated in FIG. 7. Further, as shown in FIG. 6, the site acquisition unit 10*b* outputs the region 25 of the acquired site 22 to the region-of-interest selection unit 10*c*.

The region-of-interest selection unit 10*c* is configured to select the region-of-interest 27 from the region 25 of the site 22 acquired by the site acquisition unit 10*b*. Specifically, the region-of-interest selection unit 10*c* reads the imaging program 20 from the storage unit 4. The region-of-interest selection unit 10*c* acquires the region 25 of the site 22 corresponding to the imaging region 21 as the region 25*e* to be selected as a region-of-interest 27 by the imaging program 20. In this embodiment, as illustrated in FIG. 4, the X-ray image 80 captures four sites 22: a bone tissue 22*a*, a soft tissue 22*b*, an artifact 22*c*, and a background 22*d*. Therefore, there are also four regions 25 of the sites 22 that the site acquisition unit 10*b* acquires. The region-of-interest selection unit 10*c* acquires a region of one site 22 corresponding to the imaging region 21 as the region 25 to be selected as the region-of-interest 27 from among the region 25 of the four sites 22. As shown in FIG. 6, the region-of-interest selection unit 10*c* outputs the region 25*e* to be selected as the region-of-interest 27 to the first pixel value acquisition unit 10*h*. In other words, in the first configuration, the region-of-interest selection unit 10*c* outputs the region 25*e* to be selected as a region-of-interest 27 as a region-of-interest 27.

The first pixel value acquisition unit 10*h* acquires a region-of-interest 27 from the region-of-interest selection unit 10*c*. The first pixel value acquisition unit 10*h* acquires the first pixel value 23, based on the acquired region-of-interest 27. Specifically, the first pixel value acquisition unit 10*h* acquires the first pixel value 23 as a representative value of the pixel value of the region-of-interest 27. The first pixel value acquisition unit 10*h* outputs the acquired first pixel value 23 to the X-ray condition adjustment unit 10*d*.

The X-ray condition adjustment unit 10*d* acquires the first pixel value 23 input from the first pixel value acquisition unit 10*h*. Further, the X-ray condition adjustment unit 10*d* reads the ideal pixel value 24 from the storage unit 4. The X-ray condition adjustment unit 10*d* is configured to adjust the conditions of the X-rays irradiated from the X-ray source 1, based on the first pixel value 23, which is the pixel value in the region-of-interest 27 selected by the region-of-interest selection unit 10*c*. Specifically, the X-ray condition adjustment unit 10*d* is configured to adjust the X-ray conditions so that the first pixel value 23 approaches the ideal pixel value 24. The X-ray condition adjustment unit 10*d* outputs a value 12 of the tube voltage that the first pixel value 23 approaches the ideal pixel value 24 to the device controller 8.

The device controller 8 adjusts the tube voltage, based on the value 12 of the tube voltage input from the X-ray condition adjustment unit 10*d*.

Next, the second configuration for the processor 10 to set the region-of-interest 27 will be described. Note that the configuration up to the point where the region-of-interest selection unit 10*c* acquires the region 25 of the site 22 and the imaging program 20 is the same as in the first configuration described above, and therefore, the detailed description will be omitted.

In the second configuration, it is configured such that the site designation reception unit 10*e* accepts the designation of the region 25 of the site 22 to be selected as a region-of-interest selection unit 27, based on the input of the input reception unit 5. Specifically, the site designation reception unit 10*e* acquires a site 22*e* to be selected as a region-of-interest selection unit 27, based on the operation input 50*a* for the site designation input entered from the input reception unit 5. In this embodiment, the operation input for the user to select the site 22 on the site selection screen 31 shown in FIG. 5 is the operation input 50*a* to specify the site 22. The site designation reception unit 10*e* outputs the site 22*e* to be selected as a region-of-interest 27 to the region-of-interest selection unit 10*c*.

The region-of-interest selection unit 10*c* selects a region 25*e* to be selected as a region-of-interest 27 among the regions 25 of a plurality of sites 22. In other words, the region-of-interest selection unit 10*c* selects the region 25 of the site 22*e* designated by the site designation reception unit 10*e* as the region-of-interest 27. The region-of-interest selection unit 10*c* then outputs the region 25*e* to be selected as a region-of-interest 27 to the first pixel value acquisition unit 10*h*, as a region-of-interest 27. In other words, in the second configuration, the region-of-interest setting unit 10*c* selects, not the region 25 of the site 22 set in advance, but the region 25 (region 22*e* to be selected as a region-of-interest unit 27) of the site 22 selected by the user, as a region-of-interest 27.

In the second configuration, the configuration for the first pixel value acquisition unit 10h to acquire the first pixel value 23 and the configuration for the X-ray condition adjustment unit 10d to adjust the X-ray conditions are the same as those in the first configuration. Therefore, the detailed description will be omitted.

Next, the third configuration for the processor 10 to set the region-of-interest 27 will be described. Note that the configuration up to the point where the region-of-interest selection unit 10c acquires the region 25 of the site 22 and the imaging program 20 is acquired is the same as in the first configuration described above. Therefore, the detailed description will be omitted.

In the third configuration, it is a configuration for the processor 10 to set the region-of-interest 27 when a rectangular region 26 is set by the user's operation input. In the third configuration, the region-of-interest selection unit 10c outputs to the region 25e to be selected as a region-of-interest 27 to the region-of-interest setting unit 10g.

Further, the rectangular region setting unit 10f is configured to set a rectangular region 26 in the X-ray image 80 based on the input operation entered by the input reception unit 5. Specifically, the rectangular region setting unit 10f sets a rectangular region 26 in the X-ray image 80, based on the input operation input 50b for the rectangular region 26 input from the input reception unit 5. The rectangular region setting unit 10f outputs the set rectangular region 26 to the region-of-interest setting unit 10g.

The region-of-interest setting unit 10g is configured to set the rectangular region 26 set by the rectangular region setting unit 10f as the region-of-interest 27, based on the operation input received by the input reception unit 5. Furthermore, in the case where the region 25e to be selected as a region-of-interest 27 is input from the region-of-interest selection unit 10c, and a rectangular region 26 is input from the rectangular region setting unit 10f, the region-of-interest setting unit 10g set the region-of-interest 27, based on the region 25e to be selected as a region-of-interest 27 and the rectangular region 26. The region-of-interest setting unit 10g outputs the set region-of-interest 27 to the first pixel value acquisition unit 10h. The configuration for the first pixel value acquisition unit 10h to acquire the first pixel value 23 and the configuration for the X-ray condition adjustment unit 10d to adjust the X-ray conditions are the same as those in the first configuration. Therefore, the detailed description will be omitted.

Note that the region 25e to be selected as a region-of-interest 27 is a region 25e selected as a candidate for a region-of-interest 27 out of the regions 25 of the plurality of sites 22. In the first and second configurations described above, the region 25e to be selected as a region-of-interest 27 is set as a region-of-interest 27 as it is. Furthermore, in the third configuration above, the region-of-interest 27 is set, based on the region 25e to be selected as a region-of-interest 27 and the rectangular region 26.

(Selection of Region-of-Interest and Acquisition of First Pixel Value)

Next, referring to FIG. 7, the configuration for the region-of-interest selection unit 10c to select a region-of-interest 27 and the configuration for the first pixel value acquisition unit 10h to acquire the first pixel value 23 based on the region-of-interest 27 selected by the region-of-interest selection unit 10c will be described. Note that the configuration described in FIG. 7 is the configuration for the processor 10 to select the region-of-interest 27 and the configuration to acquire the first pixel value 23 by the first configuration will be described above.

As shown in FIG. 7, the X-ray image 80 generated by the image generation unit 10a (see FIG. 2) is input to the site acquisition unit 10b.

The site acquisition unit 10b acquires a label image 80a in which the sites 22 appearing in the X-ray image 80 are classified by the trained model 11. The label image 80a is an image with labels different for each of the sites 22. In the example shown in FIG. 7, the label image 80a is an image with different label values for the region 25a of the bone tissue 22a, the region 25b of the soft tissue 22b, the region 25c of the artifact 22c, and the region 25d of the background 22d. In the example shown in FIG. 7, for convenience, the region 25a of the bone tissue 22a, the region 25c of the artifact 22c, and the region 25d of the background 22d are hatched differently from each other.

The label image 80a acquired by the site acquisition unit 10b is input to the region-of-interest selection unit 10c.

The region-of-interest selection unit 10c selects one of the sites 22 out of the sites 22 appearing in the label image 80a as a region-of-interest 27. In the example shown in FIG. 7, since the region 25a of the bone tissue 22a is set as the site 22 to be selected in advance as a region-of-interest 27, the region-of-interest selection unit 10c selects the region 25a of the bone tissue 22a as a region-of-interest 27.

In this embodiment, in the case where the non-region-of-interest is included inside the region 25 (see FIG. 6) of the site 22, the region-of-interest selection unit 10c is configured to select the region in which the non-region-of-interest is excluded from the region 25 of the site 22, as a region-of-interest 27. In other words, in the case where a site 22 other than the site 22 that the user desires to visually recognize is included inside the site 22 that the user desires to visually recognize, the region-of-interest selection unit 10c selects the region 25 of the site 22 in which the site 22 other than the site 22 that the user desires to visually recognize is excluded as a region-of-interest selection unit 27.

For example, as shown in FIG. 7, in the case where the region 25c of the artifact 22c is included inside the region 25a of the bone tissue 22a, the region-of-interest selection unit 10c selects a region in which the region 25c of the artifact 22c is excluded from the region 25a of the bone tissue 22a, as a region-of-interest 27. Note that the non-interest region is referred to as a region other than the region-of-interest 27 out of the regions 25 of a plurality of sites 22. In other words, the non-region-of-interest region is referred to as a site 22 other than the site 22 set in advance for each imaging region 21 (see FIG. 1) or a region 25 of a site 22 other than the site 22e (see FIG. 6) to be selected as a region-of-interest 27.

Further, the label image 80b in which the region-of-interest 27 is selected by the region-of-interest selection unit 10c is input to the first pixel value acquisition unit 10h. The first pixel value acquisition unit 10h acquires the pixel value within the region-of-interest 27 in the input label image 80b as the first pixel value 23. Specifically, the first pixel value acquisition unit 10h acquires the average pixel value in the region-of-interest 27, as a representative value of the pixel values in the region-of-interest 27. In other words, the first pixel value acquisition unit 10h acquires the average pixel value within the region-of-interest 27 as the first pixel value 23.

Further, the X-ray condition adjustment unit 10d (see FIG. 2) is configured to adjust the X-ray conditions, based on the first pixel value 23 of the region-of-interest 27 in which the non-region-of-interest is excluded from the region 25 of the site 22.

<Setting of Region-of-Interest and Acquisition of First Pixel Value>

Next, referring to FIG. 8, the configuration in which the region-of-interest setting unit 10g sets the region-of-interest 27 and the first pixel value acquisition unit 10h acquires the first pixel value 23 based on the region-of-interest 27 set by the region-of-interest setting unit 10g will be described. Note that the example shown in FIG. 8 is a configuration in which the region 25e of the site 22e to be selected as a region-of-interest 27 is set by the region-of-interest selection unit 10c (see FIG. 2) and the region-of-interest 27 is set in the case where there is an operation input (the operation input 50b (see FIG. 6) for the rectangular region 26), and the third configuration for acquiring the first pixel value 23.

Figure 8:
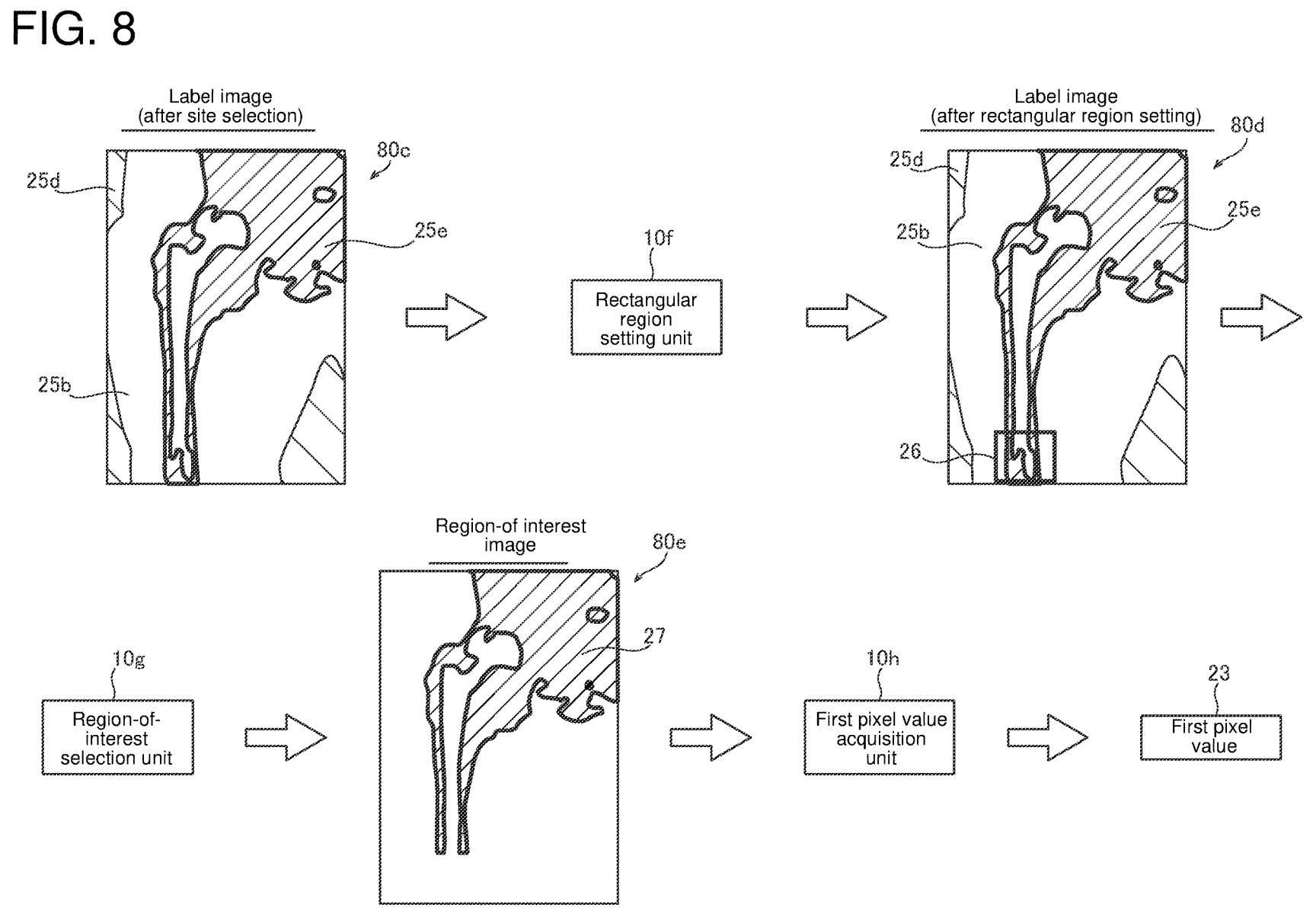

As shown in FIG. 8, the label image 80c with the region 25e selected by the region-of-interest selection unit 10c (see FIG. 2) is input to the rectangular region setting unit 10f. The rectangular region setting unit 10f sets the rectangular region 26 on the label image 80c, based on the operation input 50b (see FIG. 6) of the rectangular region 26 input from the input reception unit 5 (see FIG. 6). Specifically, the rectangular region setting unit 10f sets a rectangular region 26 of a predetermined size at a position designated by the user, based on the operation input 50b of the rectangular region 26. As a result, the rectangular region setting unit 10f acquires the label image 80d with a rectangular region 26 set for the label image 80c. Note that the rectangular region setting unit 10f may be configured to set a rectangular region 26 of the size specified by the user at the position specified by the user.

The rectangular region setting unit 10f outputs the acquired label image 80d to the region-of-interest setting unit 10g.

In the case where a rectangular region 26 is set and that one of the regions of the sites 22 is selected, the region-of-interest setting unit 10g is configured to set, as a region-of-interest 27, the region in which the rectangular region 26 is excluded from the region 25e of the selected site 22, or both the region 25e of the selected site 22 and the rectangular region 26.

The example shown in FIG. 8 is a configuration in which the region-of-interest setting unit 10g sets the region in which the rectangular region 26 is excluded from the region 25e of the selected site 22 as the region-of-interest 27. The region-of-interest setting unit 10g acquires the region-of-interest image 80e in which the region in which the rectangular region 26 is excluded from the region 25e of the selected site 22 is set as a region-of-interest 27. Further, the region-of-interest setting unit 10g outputs the region-of-interest image 80e to the first pixel value acquisition unit 10h.

The first pixel value acquisition unit 10h acquires the average pixel value within the region-of-interest 27 in the region-of-interest image 80e as the first pixel value 23.

<Adjustment Processing of X-Ray Conditions>

Figure 9:
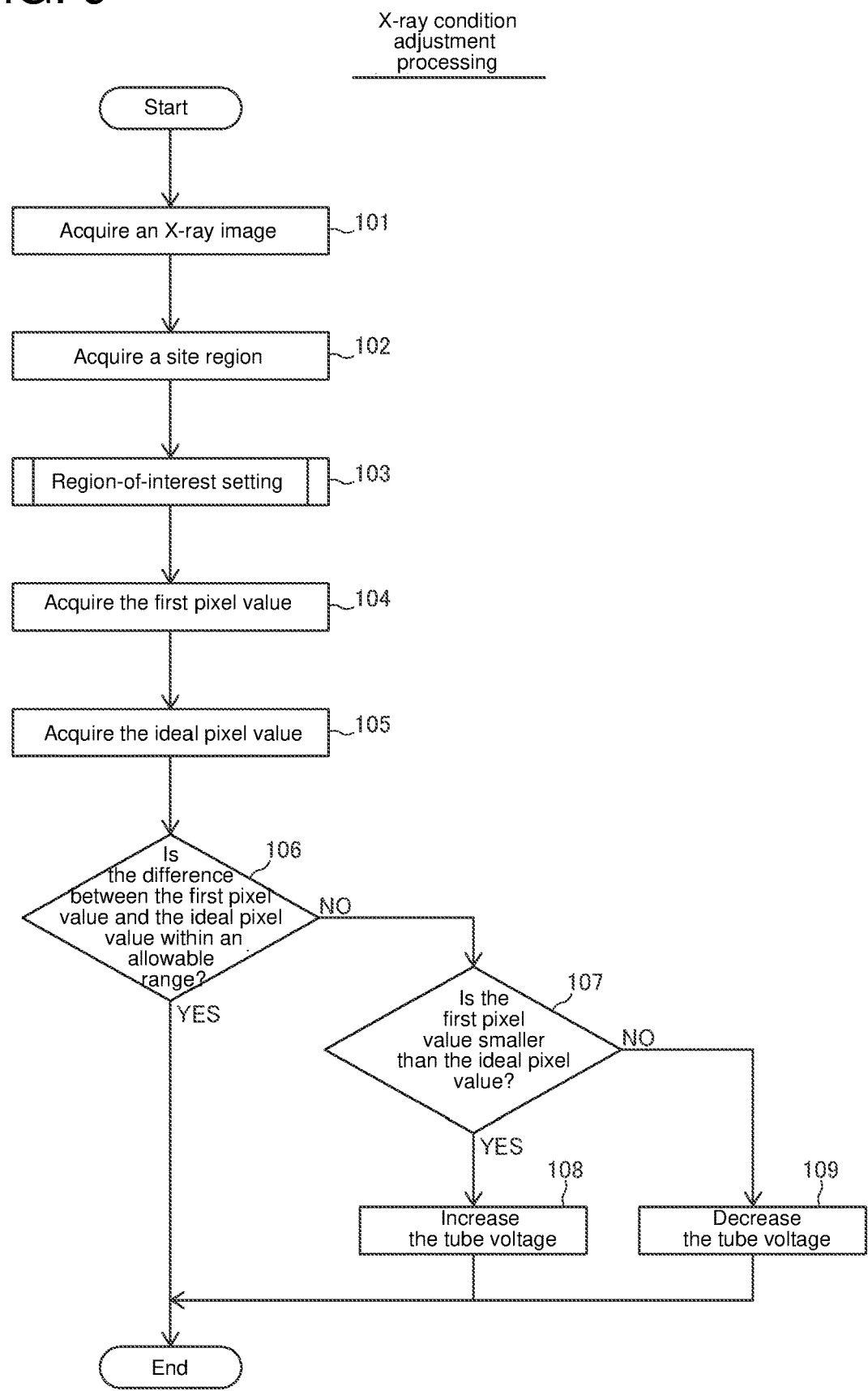
FIG. 9 is a flowchart describing the processing for a processor according to one embodiment to adjust the X-ray conditions.

Next, referring now to FIG. 9, the processing for the processor 10 (see FIG. 6) to adjust the X-ray conditions will be described.

Figure 6:
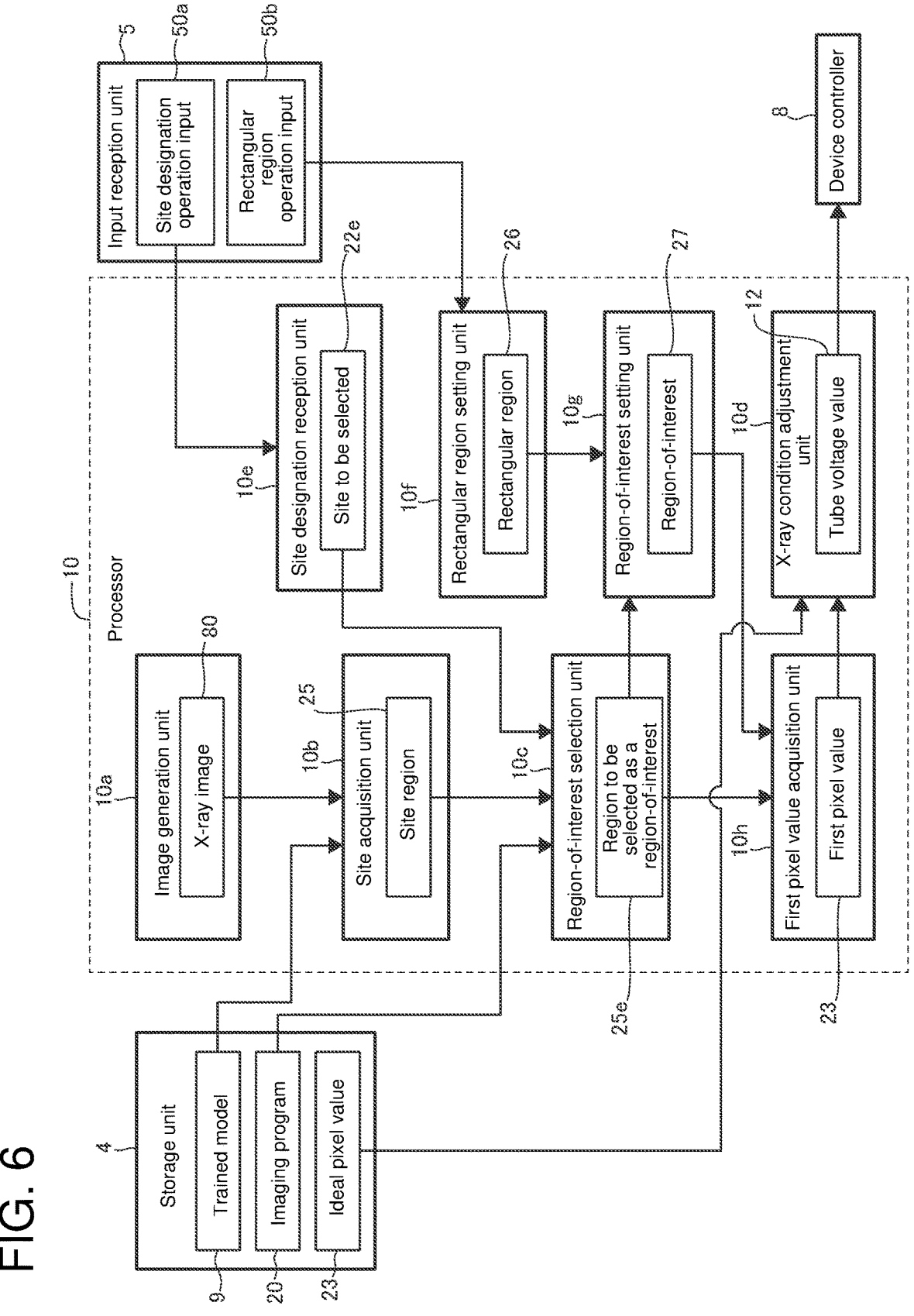
FIG. 6 is a block diagram describing the configuration for the processor to adjust the X-ray conditions according to one embodiment.

In Step 101, the site acquisition unit 10b (FIG. 6) acquires the X-ray image 80 (FIG. 6) generated by the image generation unit 10a (FIG. 6).

In Step 102, the site acquisition unit 10b acquires the region 25 (see FIG. 6) of each site 22 (see FIG. 1) appearing in the X-ray image 80 using the trained model 11 (see FIG. 6). In this embodiment, the site acquisition unit 10b acquires the region 25a (FIG. 7) of the bone tissue 22a (FIG. 7), the region 25b (FIG. 7) of the soft tissue 22b (FIG. 7), the region

25c (FIG. 7) of the artifact 22c (FIG. 7), and the region 25d (FIG. 7) of the background 22d (FIG. 7).

In Step 103, the region-of-interest selection unit 10c (see FIG. 6) or the region-of-interest setting unit 10g (see FIG. 6) selects a region-of-interest 27 (see FIG. 6), based on the imaging program 20 and the region 25 of the site 22. The details of the processing for the region-of-interest selection unit 10c or the region-of-interest setting unit 10g to select the region-of-interest 27 will be described later.

In Step 104, the first pixel value acquisition unit 10h (see FIG. 6) acquires the first pixel value 23 (see FIG. 6). Specifically, the first pixel value acquisition unit 10h acquires the average pixel value within the region-of-interest 27 as the first pixel value 23.

In Step 105, the X-ray condition adjustment unit 10d (see FIG. 6) acquires the ideal pixel value 24 (see FIG. 6) from the storage unit 4. Note that either the processing of Step 104 or the processing of Step 105 may be performed first.

In Step 106, the X-ray condition adjustment unit 10d determines whether the difference between the first pixel value 23 and the ideal pixel value 24 falls within the tolerance range. In the case where the difference between the first pixel value 23 and the ideal pixel value 24 falls within the tolerance range, the processing is terminated. In other words, in the case where the difference between the first pixel value 23 and the ideal pixel value 24 falls within the tolerance range, the X-ray condition adjustment unit 10d does not adjust the X-ray conditions. Note that the difference between the first pixel value 23 and the ideal pixel value 24 falls within a tolerance is a concept including the case in which the pixel values are in perfect agreement with each other and the case in which the difference between the first pixel value 23 and the ideal pixel value 24 falls within a predetermined range set in advance.

In the case where the first pixel value 23 and the ideal pixel value 24 are not equal, the processing proceeds to Step 107.

In Step 107, the X-ray condition adjustment unit 10d determines whether the first pixel value 23 is less than the ideal pixel value 24. In the case where the first pixel value 23 is less than the ideal pixel value 24, the processing proceeds to Step 108. In the case where the first pixel value 23 is greater than the ideal pixel value 24, the processing proceeds to Step 109.

In Step 108, the X-ray condition adjustment unit 10d increases the value 12 of the tube voltage. In this embodiment, the X-ray condition adjustment unit 10d, for example, increases the value 12 of the tube voltage by a preset value. The preset value is, for example, 10 kV (kilovolts). Thereafter, the processing is terminated.

Furthermore, in the case where the processing proceeds from Step 107 to Step 109, in Step 109, the X-ray condition adjustment unit 10d decreases the value 12 of the tube voltage. In this embodiment, the X-ray condition adjustment unit 10d, for example, decreases the value 12 of the tube voltage by a preset value. The preset value is, for example, 10 kV (kilovolts). Thereafter, the processing is terminated.

In this embodiment, the processor 10 performs the above processing of Step 101 to Step 109 for each frame of acquiring an X-ray image 80, which is a moving image. Further, in this embodiment, as described above, the processor 10 increases or decreases the value 12 of the tube voltage in a stepwise manner so that the first pixel value 23 approaches the ideal pixel value 24, and repeatedly adjusts the X-ray conditions until the difference between the first pixel value 23 and the ideal pixel value 24 falls within a tolerance range.

13
14

<Setting Processing of Region-of-Interest>

Next, referring to FIG. 10, the processing for the processor 10 (see FIG. 6) to set the region-of-interest 27 will be described.

In Step 103a, the site designation reception unit 10e (see FIG. 6) determines whether a site designation operation input 50a (see FIG. 6) has been performed. In the case where the site designation operation input 50a has been performed, the processing proceeds to Step 103b. In the case where no site designation operation input 50a has been performed, the processing proceeds to Step 103e.

In Step 103b, the rectangular region setting unit 10f determines whether an input operation input 50b (see FIG. 6) for setting a rectangular region 26 (see FIG. 8) has been performed. In the case where an input operation input 50b for setting the rectangular region 26 has been performed, the processing proceeds to Step 103c. In the case where no input operation input 50b for setting the rectangular region 26 has been performed, the processing proceeds to Step 103d.

In Step 103c, the region-of-interest setting unit 10g (see FIG. 6) sets the region-of-interest 27, based on the region 25e (see FIG. 6) of the site 22e (see FIG. 6) to be selected as a region-of-interest 27 specified by the site designation operation input 50a and the rectangular region 26 (see FIG. 6). Thereafter, the processing proceeds to Step 104.

In the case where the processing has proceeded from Step 103b to Step 103d, in Step 103d, the site acquisition unit 10b (see FIG. 6) selects, from the region 25 (see FIG. 6) of the site 22 (see FIG. 1), the region 25e (see FIG. 6) of a site 22e (see FIG. 6) to be selected, as specified by the site designation operation input 50a (see FIG. 6), as the region-of-interest 27. Thereafter, the processing proceeds to Step 104.

In the case where the processing has proceeded from Step 103a to Step 103e, in Step 103e, the site acquisition unit 10b selects, as a region-of-interest 27, the preset region out of the region 25 of the site 22. Specifically, the site acquisition unit 10b selects, as a region-of-interest 27, a preset region out of the region 25 of the site 22, based on the imaging program 20 stored in the storage unit 4 and the imaging region 21. Thereafter, the processing proceeds to Step 104.

Effects of this Embodiment

In this embodiment, the following effects can be obtained.

In this embodiment, as described above, the X-ray imaging apparatus 100 is provided with the X-ray source 1 for irradiating the patient 90 with X-rays, the X-ray detector 2 for detecting the X-rays emitted from the X-ray source 1, the image generation unit 10a for generating the X-ray image 80 based on the detection signal of the X-rays detected by the X-ray detector 2, the site acquisition unit 10b for acquiring the region 25 for each site 22 in the X-ray image 80, based on the trained model 11 that has been trained to classify the sites 22 reflected in the X-ray image 80, the region-of-interest selection unit 10c for selecting the region-of-interest selection unit 27 from among the regions 25 of the site 22 acquired by the site acquisition unit 10b, and the X-ray condition adjustment unit 10d for adjusting the conditions of the X-rays emitted from the X-ray source 1, based on the first pixel value 23, which is the pixel value in the region-of-interest 27 selected by the region-of-interest selection unit 10c.

With this, X-ray conditions are adjusted based on the first pixel value 23 that is a pixel value in the region-of-interest 27 among regions classified by multiple sites 22 appeared in the X-ray image 80, and therefore, it is possible to suppress the inclusion of pixel values of sites 22 other than the region-of-interest 27 in the first pixel value 23. Therefore, it becomes possible to adjust the X-ray conditions based solely on the first pixel value 23, thereby making it easier to adjust the X-ray conditions to suit the site 22 that the user desires to visually recognize. As a result, by enabling the user to easily adjust the X-ray conditions to suit the site 22 that the user desires to visually recognize, it is possible to prevent the deterioration of the visibility of the site 22 that the user desires to visually recognize.

Further, in the above-described embodiment, the following further effects can be obtained by configuring as follows.

In other words, in this embodiment, as described above, the site acquisition unit 10b is configured to acquire, as the region 25 of the site 22, following regions divided into at least two regions out of the region 25a of the bone tissue 22a, the region 25b of the soft tissue 22b, the region 25c of the artifact 22c, and the region 25d of the background 22d. This makes it possible to provide an X-ray imaging apparatus capable of adjusting the X-ray conditions to suit the user's desired region out of the region 25a of the bone tissue 22a, the region 25b of the soft tissue 22b, the region 25c of the artifact 22c, and the region 25d of the background 22d.

Further, in this embodiment, as described above, the region-of-interest selection unit 10c is configured to select the region in which the non-region-of-interest is excluded from the region 25 of the site 22, as a region-of-interest 27 in the case where a non-interest region is included inside the region 25 of the site 22, and the X-ray condition adjustment unit 10d is configured to adjust the X-ray conditions, based on the first pixel value 23 of the region-of-interest 27 in which the non-interest region is excluded from the region-of-interest 25 of the site 22. With this, even in the case where a non-region-of-interest is included inside the region 25 of the site 22, it is possible to suppress the inclusion of the pixel value of the non-region-of-interest in the pixel value acquired as the first pixel value 23. As a result, it is possible to suppress the deterioration of the adjustment accuracy of the X-ray conditions due to the pixel values of the non-region-of-interests.

Furthermore, in this embodiment, as described above, it is further provided with the storage unit 4 for storing the imaging region 21 of the patient 90 and the region 25 of the site 22 set in advance as the region-of-interest 27 in an associated state. The region-of-interest selection unit 10c is configured to select the region 25 of the site 22 corresponding to the imaging region 21 as the region-of-interest 27. With this, unlike the configuration in which the user selects both the imaging region 21 and the region-of-interest 27 without selecting the site 22, the user can select the region-of-interest 27 without selecting the site 22, by selecting only the imaging region 21. As a result, it is possible to suppress the increase in the number of operation input operations by the user when capturing the X-ray image 80, thereby suppressing the complexity of the operation when capturing the X-ray image 80.

Further, in this embodiment, as described above, the trained models 11 include a plurality of trained models 11 for each imaging region 21 that have been trained to classify the site 22 according to the imaging region 21, and the site acquisition unit 10b is configured to acquire the region 25 of the site 22 in the X-ray image 80 based on the trained models 11 according to the imaging region 21 out of the plurality of the trained models 11. With this, it is possible to perform training suitable for the imaging region 21 and the site 22 for each imaging region 21 on the trained model 11. As a result, compared with the configuration in which the classification of the sites 22 according to multiple imaging regions 21 is to be trained for a single trained model 11, the deterioration of the classification accuracy of the sites 22 in each trained model 11 can be suppressed.

Further, in this embodiment, as described above, it is further provided with the input reception unit 5 for receiving the user's operation input, and the site designation reception unit 10*e* for receiving the designation of the region 25 of the site 22 to be selected as a region-of-interest selection unit 27, based on the input of the input reception unit 5. With this, for example, in the case where the site 22*e* to be selected as a region-of-interest 27 is set in advance for each of the imaging regions 21, the user can still select the desired site 22 as a region-of-interest 27. As a result, it becomes possible to increase the degree of freedom in selecting the site 22*e* to be selected as a region-of-interest 27, thus improving the user's convenience (usability).

Furthermore, in this embodiment, as described above, it is further provided with the input reception unit 5 for receiving the user's operation input, the rectangular region setting unit 10*f* for setting a rectangular region 26 in the X-ray image 80 based on the operation input received by the input reception unit 5, and the region-of-interest setting unit 10*g* for the rectangular region 26 to set by the rectangular region setting unit 10*f* as a region-of-interest 27, based on the operation input received by the input reception unit 5 as the region-of-interest 27. With this, for example, in the case where it is possible to include only one site 22 inside a single rectangular region 26, the X-ray conditions can be adjusted without having to classify the site 22 using the trained model 11. As a result, it is possible to suppress the increase in the processing load of the processor 10 due to the classification of the sites 22 by the trained model 11.

Further, in this embodiment, as described above, the region-of-interest setting unit 10*g* is configured such that in the case where the rectangular region 26 is set and that one of the regions of the site 22 is selected, the region in which the rectangular region 26 is excluded from the region 25*e* of the selected site 22, or both the region 25*e* of the selected site 22 and the rectangular region 26 is selected, the region in which the rectangular region 26 is excluded from the selected site 22 is set as a region-of-interest 27. With this, the region in which the rectangular region 26 is excluded from the selected 22 is set as a region-of-interest 27. Thus, for example, in the case where the trained model 11 has low accuracy in classifying the sites 22 and that the region 25 of the other site 22 is included in the region 25*e* of the selected site 22, by setting the rectangular region 26 in the region in which the other site 22 is included, out of the region 25*e* of the selected site 22, it is possible to further suppress that non-region-of-interests are included in the region-of-interest 27. As a result, it is possible to suppress the deterioration of the adjustment accuracy of the X-ray conditions. Further, both the region 25*e* of the selected site 22 and the rectangular region 26 are set as region-of-interest 27, a region different from the selected site 22 can also be included in the region-of-interest 27. As a result, not only the region 25 of the site 22 classified by the trained model 11 but also the rectangular region 26 set by the user can be used as the region-of-interest 27, which improves the user's convenience (usability).

Further, in this embodiment, as described above, it is further provided with the storage unit 4 for storing ideal pixel values 24, which are ideal pixel values set in advance for each imaging unit 21 of the patient 90, and the X-ray condition adjustment unit 10*d* is configured to adjust the X-ray conditions so that the first pixel value 23 approaches the ideal pixel value 24. With this, the X-ray conditions are adjusted so as to approach the ideal pixel value 24, which is the ideal pixel value in the imaging region 21, which can improve the image quality of the site 22 selected as a region-of-interest 27 in the X-ray image 80.

Further, in this embodiment, as described above, the X-ray tube conditions include, at least a tube voltage. With this, by adjusting the tube voltage that contributes to the intensity and energy of the X-rays emitted from the X-ray source 1, it is possible to make the X-ray source 1 irradiate X-rays with an intensity and energy suitable for the region-of-interest 27.

Modifications

Note that the embodiments disclosed here should be considered illustrative and not restrictive in all respects. It should be noted that the scope of the present invention is indicated by claims and is intended to include all modifications (modified examples) within the meaning and scope of the claims and equivalents.

In this embodiment, an example of the configuration is shown in which the site acquisition unit 10*b* acquires, as the region 25 of the site 22, at least two of the following regions: the region 25*a* of the bone tissue 22*a*, the region 25*b* of the soft tissue 22*b*, the region 25*c* of the artifact 22*c*, and the region 25*d* of the background 22*d*, but the present invention is not limited thereto. In the present invention, the site acquisition unit 10*b* may be configured to acquire a region classified as a region that includes regions other than the four regions described above (e.g., the region of a blood vessel in which a contrast agent is administered).

Further, in the above embodiment, an example of a configuration is shown in which the X-ray imaging apparatus 100 is provided with a plurality of trained models 11 that have been trained to classify sites 22 according to an imaging region 21, but the present invention is not limited thereto. In the present invention, the X-ray imaging apparatus 100 may be equipped with a single trained model that has been trained to classify sites 22 according to a plurality of imaging regions 21.

Further, in the above embodiment, an example of a configuration is shown in which the X-ray imaging apparatus 100 is equipped with the site designation reception unit 10*e*, but the present invention is not limited thereto. In the present invention, the X-ray imaging apparatus 100 does not need to have the site designation reception unit 10*e*. However, in the case where the X-ray imaging apparatus 100 is not equipped with the site designation reception unit 10*e*, it is not possible to adjust the X-ray conditions to suit a site other than the site 22 set in advance in accordance with the imaging region 21. Therefore, the X-ray imaging apparatus 100 is preferably equipped with the site designation reception unit 10*e*.

Furthermore, in the above embodiment, an example of a configuration is shown in which the X-ray imaging apparatus 100 is equipped with the rectangular region setting unit 10*f* and the rectangular region-of-interest setting unit 10*g*, but the present invention is not limited thereto. For example, the X-ray imaging apparatus 100 may not have the rectangular region setting unit 10*f* and the region-of-interest setting unit 10*g*. However, in the case where the X-ray imaging apparatus 100 is configured not to have the rectangular region setting unit 10*f* and the region-of-interest setting unit 10*g*, the degree of freedom in setting the region-of-interest 27 may be reduced. Therefore, the X-ray imaging apparatus 100 is preferably equipped with the rectangular region setting unit 10*f* and the region-of-interest setting unit 10*g*.

Further, in the above embodiment, an example of a configuration is shown in which the region-of-interest setting unit 10g sets, as the region-of-interest 27, the region in which the rectangular region 26 is excluded from the region 25e of the selected site 22, but the present invention is not limited thereto. In the present invention, for example, the region-of-interest setting unit 10g may be configured to set both the region 25e of the selected site 22 and the rectangular region 26, as a region-of-interest 27.

Further, in the above embodiment, an example of a configuration is shown in which the region-of-interest setting unit 10g sets, as the region-of-interest 27, the region in which the rectangular region 26 is excluded from the region 25e of the selected site 22, but the present invention is not limited thereto. For example, the region-of-interest setting unit 10g may be configured to set the rectangular region 26 set by the user's operation input, as a region-of-interest 27.

Further, in the above embodiment, an example of a configuration is shown in which the X-ray condition adjustment unit 10d adjusts the value 12 of the tube voltage as the X-ray conditions, but the invention is not limited thereto. In the present invention, for example, the X-ray condition adjustment unit 10d may be configured to adjust at least one of the values of the tube current and the X-ray irradiation time, as the X-ray conditions.

Further, in the above embodiment, an example of a configuration is shown in which the site designation reception unit 10e sets the site 22 selected by the user on the site selection screen 31 as the site 22e to be selected as a region-of-interest 27, but the present invention is not limited thereto. In the present invention, the site designation reception unit 10e may be configured, for example, to set the site 22 selected by the user in the X-ray image 80 as the site 22e to be selected, as a region-of-interest 27.

Further, in the above embodiment, an example of a configuration is shown in which the X-ray imaging apparatus 100 is a so-called X-ray fluoroscopic imaging apparatus that captures images 80 as a moving image, but the present invention is not limited thereto. The X-ray imaging apparatus 100 may be configured as a so-called general imaging apparatus that captures X-ray images 80 as still images.

Further, in the above embodiment, an example of a configuration is shown in which the X-ray imaging apparatus 100 is installed in an examination room or the like, but the present invention is not limited thereto. In the present invention, for example, the X-ray imaging apparatus 100 may be configured as a so-called circular X-ray imaging apparatus designed to be moved to a hospital room or other location to perform X-ray imaging.

ASPECTS

It would be understood by those skilled in the art that the exemplary embodiments described above are specific examples of the following aspects.

(Item 1)

An X-ray imaging apparatus comprising:

an X-ray source configured to irradiate a patient with X-rays;

an X-ray detector configured to detect the X-rays emitted from the X-ray source;

an image generation unit configured to generate an X-ray image based on a detection signal of the X-rays detected by the X-ray detector;

a site acquisition unit configured to acquire a region for each site in the X-ray image, based on a trained model that has been trained to classify sites captured in the X-ray image;

a region-of-interest selection unit configured to select a region-of-interest from a region of the site acquired by the site acquisition unit; and an X-ray condition adjustment unit configured to adjust conditions of X-rays emitted from the X-ray source, based on a first pixel value that is a pixel value inside the region-of-interest selected by the region-of-interest selection unit.

(Item 2)

The X-ray imaging apparatus as recited in the above-described Item 1, wherein the site acquisition unit is configured to acquire a region classified into at least two regions as a region of the site, the at least two regions including a bone tissue region, a soft tissue region, an artifact region, and a background region.

(Item 3)

The X-ray imaging apparatus as recited in the above-described Item 2, wherein in a case where a non-region-of-interest is included inside the region of the site, the region-of-interest selection unit is configured to select a region in which the non-region-of-interest is excluded from the region of the site, as the region-of-interest, and wherein the X-ray condition adjustment unit is configured to adjust conditions of the X-rays, based on the first pixel value of the region-of-interest in which the non-region-of-interest is excluded from the region of the site.

(Item 4)

The X-ray imaging apparatus as recited in the above-described Item 2, further comprising:

a storage unit configured to store the imaging region of the patient and the region of the site set in advance as the region-of-interest in an associated state, wherein the region-of-interest selection unit is configured to select the region of the site corresponding to the imaging region, as the region-of-interest.

(Item 5)

The X-ray imaging apparatus as recited in the above-described Item 4, wherein the trained model includes a plurality of trained models that have been trained to classify the site corresponding to the imaging region for each imaging region, and wherein the site acquisition unit is configured to acquire the region of the site in the X-ray image, based on the trained model corresponding to the imaging region out of a plurality of the trained models.

(Item 6)

The X-ray imaging apparatus as recited in the above-described Item 2, further comprising:

an input reception unit configured to receive an operation input of a user; and a site designation reception unit configured to receive a designation of the region of the site to be selected as the region-of-interest, based on an input from the input reception unit.

(Item 7)

The X-ray imaging apparatus as recited in the above-described Item 2, further comprising:

an input reception unit configured to receive an operation input of a user;

a rectangular region setting unit configured to set a rectangular region in the X-ray image, based on an operation input entered by the input reception unit; and a region-of-interest setting unit configured to set the rectangular region set by the rectangular region setting unit as the region-of-interest, based on an operation input entered by the input reception unit.

(Item 8)

The X-ray imaging apparatus as recited in the above-described Item 7, wherein in a case where the rectangular region is set and that any one of the regions in the site is selected, the region-of-interest setting unit is configured to set, as the region-of-interest, a region in which the rectangular region is excluded from the region of the selected site, or both the region of the selected site and the rectangular region.

(Item 9)

The X-ray imaging apparatus as recited in the above-described Item 1, further comprising:

a storage unit configured to store an ideal pixel value that is an ideal pixel value set in advance for each imaging region of the patient, wherein the X-ray condition adjustment unit is configured to adjust the conditions of X-rays so that the first pixel value approaches the ideal pixel value.

(Item 10)

The X-ray imaging apparatus as recited in the above-described Item 1, wherein the X-ray conditions include at least a tube voltage.

DESCRIPTION OF REFERENCE SYMBOLS

1: X-ray source
2: X-ray detector
4: Storage unit
5: Input reception unit
10a: Image generation unit
10b: Site acquisition unit
10c: Region-of-interest selection unit
10d: X-ray condition adjustment unit
10e: Site designation reception unit
10f: Rectangular region setting unit
10g Region-of-interest setting unit
11: Trained model
21: Imaging region
22: Site
22a: Bone tissue
22b: Soft tissue
22c: Artifact
22d: Background
22e: Site to be selected as a region-of-interest
23: First pixel value
24: Ideal pixel value
25: Region of a site
25a Bone tissue region
25b: Soft tissue region
25c: Artifact region
25d: Background region
25e: Region to be selected as a region-of-interest
26: Rectangular region
27: Region-of-interest
80: X-ray image
90: Patient
100: X-ray imaging apparatus

The invention claimed is:

1. An X-ray imaging apparatus comprising:

an X-ray source configured to irradiate a patient with X-rays;

an X-ray detector configured to detect the X-rays emitted from the X-ray source;

an image generation unit as a processor configured to generate an X-ray image based on a detection signal of the X-rays detected by the X-ray detector;

a region acquisition unit as the processor configured to acquire a region of a part, the region of the part having a shape of the part in the X-ray image, based on a trained model that has been trained to classify a plurality of parts captured in the X-ray image;

a region-of-interest setting unit as the processor configured to set a region-of-interest inside the region of the part acquired by the region acquisition unit as the processor; and an X-ray condition adjustment unit as the processor configured to adjust conditions of X-rays emitted from the X-ray source, based on a first pixel value that is a pixel value inside the region-of-interest set by the region-of-interest setting unit as the processor, without using a pixel value outside the region-of-interest.

2. The X-ray imaging apparatus as recited in claim 1, wherein the region acquisition unit as the processor is configured to classify regions of the X-ray image into at least two regions from among a bone tissue region, a soft tissue region, an artifact region, and a background region.

3. The X-ray imaging apparatus as recited in claim 2, wherein in a case where a non-region-of-interest is included inside the region of the part, the region-of-interest setting unit as the processor is configured to set a region in which the non-region-of-interest is excluded from the region of the part, as the region-of-interest, and wherein the X-ray condition adjustment unit as the processor is configured to adjust conditions of the X-rays, based on the first pixel value of the region-of-interest in which the non-region-of-interest is excluded from the region of the part.

4. The X-ray imaging apparatus as recited in claim 2, further comprising:

a memory configured to store an imaging region of the patient and a region of the part set in advance as the region-of-interest in an associated state, wherein the region-of-interest setting unit as the processor is configured to set the region of the part corresponding to the imaging region, as the region-of-interest.

5. The X-ray imaging apparatus as recited in claim 4, wherein the trained model includes a plurality of trained models that have been trained to classify the part corresponding to the imaging region for each of a plurality of imaging regions, and wherein the region acquisition unit as the processor is configured to acquire the region of the part in the X-ray image, based on the trained model corresponding to the imaging region out of a plurality of the trained models.

6. The X-ray imaging apparatus as recited in claim 2, further comprising:

an input device configured to receive an operation input of a user; and a part designation reception unit as the processor configured to receive a designation of the region of the part to be set as the region-of-interest, based on the operation input received by the input device.

7. The X-ray imaging apparatus as recited in claim 2, further comprising:

an input device configured to receive an operation input of a user;

a rectangular region setting unit as the processor is configured to set a rectangular region in the X-ray image, based on the operation input received by the input device, wherein the region-of-interest setting unit as the processor configured to set the rectangular region set by the rectangular region setting unit as the processor as the region-of-interest, based on the operation input received by the input device.

8. The X-ray imaging apparatus as recited in claim 2, further comprising:

an input device configured to receive an operation input of a user; and a rectangular region setting unit as the processor configured to set a rectangular region in the X-ray image, based on the operation input received by the input device, wherein the region-of-interest setting unit as the processor is configured to: set, as the region-of-interest, a region in which the rectangular region is excluded from the region of the part acquired by the region acquisition unit as the processor in a case where the rectangular region is set and that any one of the regions in the part is selected.

9. The X-ray imaging apparatus as recited in claim 2, further comprising:

an input device configured to receive an operation input of a user; and a rectangular region setting unit as the processor configured to set a rectangular region in the X-ray image, based on the operation input received by the input device, wherein the region-of-interest setting unit as the processor is configured to set, as the region-of-interest, both the region of the part acquired by the region acquisition unit as the processor and the rectangular region as the region-of-interest in a case where the rectangular region is set and that any one of the regions in the part is selected.

10. The X-ray imaging apparatus as recited in claim 1, further comprising:

a memory configured to store an ideal pixel value that is an ideal pixel value set in advance for each imaging region of the patient, wherein the X-ray condition adjustment unit as the processor is configured to adjust the conditions of X-rays so that the first pixel value approaches the ideal pixel value.

11. The X-ray imaging apparatus as recited in claim 1, wherein the conditions of X-rays include at least a tube voltage.

* * * * *